United States Patent [19]

Ogletree

[11] Patent Number: 4,808,627

[45] Date of Patent: Feb. 28, 1989

[54] METHOD OF PREVENTING OR TREATING TOXEMIA IN PREGNANCY USING A THROMBOXANE $A_2$ RECEPTOR ANTAGONIST

[75] Inventor: Martin L. Ogletree, Newtown, Pa.

[73] Assignee: E. R. Squibb & Sons, Inc., Princeton, N.J.

[21] Appl. No.: 133,838

[22] Filed: Dec. 16, 1987

[51] Int. Cl.$^4$ ............................................. A61K 31/34
[52] U.S. Cl. .................................... 514/469; 514/289; 514/308; 514/357; 514/419; 514/452; 514/557; 514/562; 514/570
[58] Field of Search ............... 514/469, 562, 570, 236, 514/308, 357, 419, 452, 557, 289

[56] References Cited

PUBLICATIONS

Takagi et al., Advances in Prostaglandin, Thromboxane, and Leukotriene Research, vol. 15-Raven Press, pp. 619–621 (1985).

Keith et al., Am. J. Obstet. Gynecol., 157(1), pp. 199–203 (1987).

Farber et al., Circulation, 78(2), pp. 450–461 (1988).

Ogletree, Martin L., "Overview of Physiological and Pathophysiological Effects of Thromboxane $A_2$", Federation Proceedings, vol. 46, No. 1, Jan. 1987, pp. 133–139.

Primary Examiner—Mary C. Lee
Assistant Examiner—Bernard I. Dentz
Attorney, Agent, or Firm—Lawrence S. Levinson; Burton Rodney

[57] ABSTRACT

A method is provided for preventing or treating toxemia during pregnancy by administering a thromboxane $A_2$ receptor antagonist before or during toxemia.

17 Claims, No Drawings

METHOD OF PREVENTING OR TREATING TOXEMIA IN PREGNANCY USING A THROMBOXANE A₂ RECEPTOR ANTAGONIST

FIELD OF THE INVENTION

The present invention relates to a method for preventing or treating toxemia in pregnancy by administering a thromboxane $A_2$ receptor antagonist to a pregnant woman.

BACKGROUND OF THE INVENTION

Ogletree, Martin L., "Overview of physiological and pathophysiological effects of thromboxane $A_2$", Federation Proceedings Vol. 46, No. 1, January, 1987, pp. 133 139, discloses in the "ABSTRACT" that there is evidence which "supports participation of $TxA_2$ and/or $TxA_2$ receptors ... in complications of pregnancy (e.g., preeclampsia) .... This evidence supports pivotal involvement of $TxA_2$ in pathophysiology and provides a strong rationale for pursuing $TxA_2$-blocking strategies in drug development." At page 134, it is indicated that "Conditions both involving increased synthesis of Tx metabolites and showing responsiveness of intervention with inhibitors of Tx synthesis are:

Platelet Activation and Thrombosis

Hypertension of pregnancy/preeclampsia". In addition, at page 135, it is indicated that preeclampsia and pregnancy-induced hypertension are associated with increased production of $TxA_2$ by the placenta and by platelets and that $TxA_2$ may be a pivotal mediator in certain complication of pregnancy.

DESCRIPTION OF THE INVENTION

In accordance with the present invention, a method is provided for preventing or treating toxemia during pregnancy in mammalian species, wherein a therapeutically effective amount of a thromboxane $A_2$ receptor antagonist is systemically administered, such as orally or parenterally, to mitigate adverse effects of thromboxane during pregnancy, for example, as may be indicated in an ovine model of pregnancy-induced hypertension, as described by Keith, J. C., Jr. et al., Am. J. Obstet. Gynecol., 157, No. 1, 199–203, 1987.

The term "toxemia" is employed herein to include preeclampsia, eclampsia, preeclamptic (eclamptic, eclamptogenic) toxemia, or hypertension in pregnancy.

The term "thromboxane $A_2$ receptor antagonist" as employed herein includes compounds which are so-called thromboxane $A_2$ receptor antagonists, thromboxane $A_2$ antagonists, thromboxane $A_2$/prostaglandin endoperoxide antagonists, TP-receptor antagonists, or thromboxane antagonists except insofar as the compound is solely an inhibitor of thromboxane synthesis.

Thromboxane $A_2$ receptor antagonists which may be employed herein include the 7-oxabicycloheptane and 7-oxabicycloheptene compounds disclosed in U.S. Pat. No. 4,537,981 to Snitman et al, especially, [1S-[1α,2β(5Z),3β(1E,3R,4S),4α]]-7-[3-(3-hydroxy-4-phenyl-1-pentenyl)-7-oxabicyclo[2.2.1]hept-2-yl]-5-heptenoic acid; the 7-oxabicycloheptane substituted aminoprostaglandin analogs disclosed in U.S. Pat. No. 4,416,896 to Nakane et al., especially, [1S-[1α,2β(5Z),3β,4α]]-7-[3-[[2-(phenylamino)carbonyl]hydrazino]methyl]-7-oxabicyclo[2.2.1]hept-2yl]-5-heptenoic acid; the 7-oxabicycloheptane substituted diamide prostaglandin analogs disclosed in U.S. Pat. No. 4,663,336 to Nakane et al, especially, [1S-[1β,2α(5Z),3α,4β]]-7-]3-[[[[(1-oxoheptyl)amino]acetyl]amino]methyl]-7- oxabicyclo[2.2.1]hept-2-yl]-5-heptenoic acid and the corresponding tetrazole, and [1S-[1α,2β(Z),3β,4α]]-7-[3-[[[[(4-cyclohexyl-1-oxobutyl)amino]acetyl]amino]methyl]-7-oxabicyclo[2.2.1]hept-2-yl]-5-heptenoic acid; the phenoxyalkyl carboxylic acids disclosed in U.S. Pat. No. 4,258,058 to Witte et al, especially 4-[2-benzenesulfamido)ethyl]phenoxyacetic acid, (BM 13,177-Boehringer Mannheim), the sulphonamidophenyl carboxylic acids disclosed in U.S. Pat. No. 4,443,477 to Witte et al, especially 4-[2-(4-chlorobenzenesulfonamido)ethyl]phenylacetic acid, (BM 13,505, Boehringer Mannheim) the arylthioalkylphenyl carboxylic acids disclosed in U.S. application Ser. No. 067,199 filed June 29, 1987, now U.S. Pat. No. 4,752,616, especially 4-(3-((4-chlorophenyl)sulfonyl)propyl)benzeneacetic acid.

Other examples of thromboxane $A_2$ receptor antagonists suitable for use herein include, but are not limited to (E)-5-[[[(pyridinyl)[3-(trifluoromethyl)phenyl]methylene]amino]oxy]pentanoic acid also referred to as R68,070-Janssen Research Laboratories, 3-[1-(4-chlorophenylmethyl)-5-fluoro-3-methylindol-2-yl]-2,2-dimethylpropanoic acid [L-655240 Merck-Frosst] Eur. J. Pharmacol. 135(2): 193, 17 Mar. 87], 5(Z)-7-([2,4,5-cis]-4-(2-hydroxyphenyl)-2-trifluoromethyl-1,3-dioxan-5yl)-heptenoic acid (ICI 185282, Brit. J. Pharmacol 90 (Proc. Suppl): 228 P-Abs., Mar. 87), 5(Z)-7-[2,2-dimethyl-4-phenyl-1,3-dioxan-cis-5yl]-heptenoic acid (ICI 159995, Brit. J. Pharmacol. 86 (Proc. Suppl): 808 P-Abs., Dec. 85), N,N'-bis[7-(3-chlorobenzeneaminosulfonyl)-1,2,3,4-tetrahydro-isoquinolyl]disulfonylimide SKF 88046, Pharmacologist 25(3): 116 Abs, 117 Abs, Aug. 83) [1α(Z)-2β,5α]-(+)-7-[5-[[(1,1'-biphenyl)-4-yl]methoxy]-2-(4-morpholinyl)-3-oxocyclopentyl]-4-heptenoic acid (AH 23848-Glaxo, Circulation 72(6): 1208, Dec. 85, levallorphan allyl bromide (CM 32,191, Sanofi, Life Sci. 31 (20-21): 2261, 15 Nov. 82), (Z,2-endo-3-oxo)-7-(3-acetyl-2-bicyclo[2.2.1]heptyl-5-hepta-3Z-enoic acid, 4phenylthiosemicarbazone (EP092-Univ. Edinburgh, Brit, J. Pharmacol. 84(3): 595, Mar. 85).

The disclosure of the above-mentioned patents, patent applications and other references are incorporated herein by reference.

In carrying out the method of the present invention, the thromboxane $A_2$ receptor antagonist may be administered systemically, such as orally or parenterally, to mammalian species, such as monkeys, dogs, cats, rats, humans, etc. during the period of pregnancy prior to or after the onset of toxemia.

The thromboxane $A_2$ receptor antagonist may be incorporated in a conventional dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

With regard to such systemic formulations, single or divided doses of from about 0.5 to about 2500 mg, preferably from about 5 to 2000 mg/one to four times daily, may be administered in systemic dosage forms as described above.

The thromboxane $A_2$ receptor antagonist may be administered throughout the period of pregnancy to inhibit the onset of toxemia or related conditions as defined above or may be administered to treat these conditions for a period until normal blood pressure is restored. Thereafter, the thromboxane A₂ receptor antagonist may be administered until pregnancy is completed.

The following Examples represent preferred embodiments of the present invention.

EXAMPLE 1

An injectable solution of thromboxane A₂ receptor antagonist for intravenous use in treating or preventing toxemia is produced as follows:

| | |
|---|---|
| [1S—[1α,2β(5Z),3β,4α]]-7-[3-[[2-(phenylamino)carbonyl]hydrazino]-methyl]-7-oxabicyclo[2.2.1]hept-2-yl]-5-heptenoic acid (SQ 29,548) | 2500 mg |
| Methyl paraben | 5 mg |
| Propyl paraben | 1 mg |
| Sodium chloride | 25 g |
| Water for injection qs. | 5 l. |

The thromboxane A₂ receptor antagonist, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains a concentration of 75 mg of active ingredient per 150 ml of solution.

EXAMPLE 2

An injectable for use in preventing or treating toxemia during pregnancy is prepared as described in Example 1 except that the thromboxane A₂ receptor antagonist employed is the phenoxyalkyl carboxylic acid 4-[2-(benzenesulfamido)ethyl]phenoxyacetic acid, disclosed in U.S. Pat. No. 4,258,058.

EXAMPLE 3

An injectable solution of thromboxane A₂ receptor antagonist for intravenous use containing [1S-[1β,2α(5Z),3α,4β]]-7-[3-[[[[(1-oxoheptyl)amino]acetyl]amino]methyl]-7-oxabicyclo[2.2.1]hept-2-yl]-5-heptenoic acid (SQ 30,741) as the thromboxane A₂ receptor antagonist is prepared as described in Example 1.

EXAMPLE 4

An injectable for use in treating or preventing toxemia is prepared as described in Example 1 except that the thromboxane A₂ receptor antagonist employed is [1S-[1α,2β(Z),3β,4α]]-7-[3-[[[[(4-cyclohexyl-1-oxobutyl)amino]acetyl]amino]methyl]-7-oxabicyclo[2,.2.1]hept-2-yl-5-heptenoic acid.

EXAMPLE 5

A thromboxane A₂ antagonist formulation suitable for oral administration is set out below.

1000 tablets each morning containing 400 mg of thromboxane A₂ receptor antagonist were produced from the following ingredients.

| | |
|---|---|
| [1S—[1β,2α(5Z),3α,4β]]-7-[3-[[[[(1-Oxoheptyl)amino]acetyl]amino]methyl]-7-oxabicyclo[2.2.1]hept-2-yl]-5-heptenoic acid (SQ 30,741) | 400 g |
| Corn starch | 50 g |
| Gelatin | 7.5 g |
| Avicel (microcrystalline cellulose) | 25 g |
| Magnesium stearate | 2.5 g |

The thromboxane A₂ receptor antagonist and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 400 mg of active ingredient.

What is claimed is:

1. A method for preventing or treating toxemia during pregnancy, in a mammalian species, which comprises administering to a mammalian species in need of such treatment an effective amount of a thromboxane A₂ receptor antagonist.

2. The method as defined in claim 1 wherein the thromboxane A₂ receptor antagonist is administered systemically.

3. The method as defined in claim 1 wherein the thromboxane A₂ receptor antagonist is administered intravenously or orally.

4. The method as defined in claim 1 wherein the thromboxane A₂ receptor antagonist is administered during toxemia.

5. The method as defined in claim 1 wherein the thromboxane A₂ receptor antagonist is administered during pregnancy prior to onset of toxemia.

6. The method as defined in claim 1 wherein the thromboxane A₂ receptor antagonist is a 7-oxabicycloheptane or a 7-oxabicycloheptene.

7. The method as defined in claim 1 wherein the thromboxane A₂ receptor antagonist is a 7-oxabicycloheptane substituted amino-prostaglandin analog.

8. The method as defined in claim 1 wherein the thromboxane A₂ receptor antagonist is a 7-oxabicycloheptane substituted diamide prostaglandin analog.

9. The method as defined in claim 1 wherein the thromboxane A₂ receptor antagonist is a phenoxyalkyl carboxylic acid.

10. The method as defined in claim 1 wherein the thromboxane A₂ receptor antagonist is a sulfonamidophenyl carboxylic acid.

11. The method as defined in claim 1 wherein the thromboxane A₂ receptor antagonist is an arylthioalkylphenyl carboxylic acid.

12. The method as defined in claim 1 wherein the thromboxane A₂ receptor antagonist is [1S-[1α,2β(5Z),3β(1E,3R,4S),4α]]-7-[3-(3-hydroxy-4-phenyl-1-pentenyl)-7-oxabicyclo[2.2.1]hept-2-yl]-5-heptenoic acid.

13. The method as defined in claim 1 wherein the thromboxane A₂ receptor antagonist has the name [1S-[1β,2α(5Z),3α,4β]]-7-[3-[[[[(1-oxoheptyl)amino]acetyl]amino]methyl]-7-oxabicyclo[2.2.1]hept-2-yl]-5-heptenoic acid or the corresponding tetrazole.

14. The method as defined in claim 1 wherein the thromboxane A₂ receptor antagonist has the name [1S-[1α,2β(Z),3β,4α]]-7-[3-[[[[(4-cyclohexyl-1-oxobutyl)-amino]acetyl]amino]methyl]-7-oxabicyclo[2.2.1]hept-2-yl]-5-heptenoic acid.

15. The method as defined in claim 1 wherein the thromboxane A₂ receptor antagonist has the name [1S-[1α,2β(5Z),3β,4α]]-7-[3-[[2-(phenylamino)carbonyl]hydrazino]methyl]-7-oxabicyclo[2.2.1]hept-2yl]-5-heptenoic acid.

16. The method as defined in claim 1 wherein the thromboxane A₂ receptor antagonist has the name 4-(3-((4-chlorophenyl)sulfonyl)propyl)benzene acetic acid.

17. The method as defined in claim 1 wherein the thromboxane A₂ receptor antagonist has the name or 4-[2-(benzenesulfamido)ethyl]phenoxyacetic acid or 4-[2-(4-chlorobenzenesulfonamido)ethyl]phenylacetic acid.

* * * * *